United States Patent
Younes et al.

(10) Patent No.: US 10,349,851 B2
(45) Date of Patent: Jul. 16, 2019

(54) METHOD, NON-TRANSITORY COMPUTER READABLE MEDIUM AND APPARATUS FOR AROUSAL INTENSITY SCORING

(71) Applicant: YRT Limited, Winnipeg, Manitoba (CA)

(72) Inventors: Magdy Younes, Winnipeg (CA); Ali Azarbarzin, Winnipeg (CA)

(73) Assignee: YRT LIMITED, Winnipeg, Manitoba (CA)

( * ) Notice: Subject to any disclaimer, the term of this patent is extended or adjusted under 35 U.S.C. 154(b) by 1238 days.

(21) Appl. No.: 14/447,048

(22) Filed: Jul. 30, 2014

(65) Prior Publication Data

US 2015/0038804 A1  Feb. 5, 2015

Related U.S. Application Data

(60) Provisional application No. 61/859,905, filed on Jul. 30, 2013.

(51) Int. Cl.
| | |
|---|---|
| *A61B 5/04* | (2006.01) |
| *A61B 5/00* | (2006.01) |
| *A61B 5/0476* | (2006.01) |
| *A61B 5/0205* | (2006.01) |
| *A61B 5/0488* | (2006.01) |

(52) U.S. Cl.
CPC ........ *A61B 5/04012* (2013.01); *A61B 5/0476* (2013.01); *A61B 5/4818* (2013.01); *A61B 5/726* (2013.01); *A61B 5/0205* (2013.01)

(58) Field of Classification Search
CPC . A61B 5/04012; A61B 5/0476; A61B 5/4818; A61B 5/726; A61B 5/0205
See application file for complete search history.

(56) References Cited

U.S. PATENT DOCUMENTS

| | | | |
|---|---|---|---|
| 2005/0154290 A1* | 7/2005 | Langleben | A61B 5/055 600/410 |
| 2005/0215847 A1* | 9/2005 | Heruth | A61B 5/0476 600/26 |
| 2006/0195041 A1* | 8/2006 | Lynn | A61B 5/412 600/538 |
| 2007/0123758 A1* | 5/2007 | Miesel | A61B 5/0205 600/301 |

(Continued)

*Primary Examiner* — Seahvosh Nikmanesh
(74) *Attorney, Agent, or Firm* — Tarolli, Sundheim, Covell & Tummino LLP

(57) ABSTRACT

A computerized method comprises statistically analyzing, using one or more processors, at least one section of a digitally recorded electroencephalography (EEG) signal that comprises an arousal segment to determine, for the arousal segment, at least one of amplitude and power at different frequencies as a function of time; selecting specified features from the results of the analysis and normalizing the selected features; and assigning, using one or more processors, an intensity scale value to the arousal segment based on the normalized selected features and a reference data set, the reference data set comprising normalized features corresponding to the normalized selected features and being generated based on a plurality of EEG signals comprising arousal segments to which intensity scale values have been assigned based on a visual inspection of the EEG signals.

21 Claims, 16 Drawing Sheets

(56) References Cited

U.S. PATENT DOCUMENTS

| | | | |
|---|---|---|---|
| 2008/0154111 A1* | 6/2008 | Wu | A61B 5/0478 600/383 |
| 2010/0028841 A1* | 2/2010 | Eatough | G09B 5/065 434/308 |
| 2011/0160545 A1* | 6/2011 | Champadi | A61B 5/4064 600/300 |
| 2012/0271372 A1* | 10/2012 | Osorio | A61B 5/7275 607/17 |

* cited by examiner

FIGURE 8
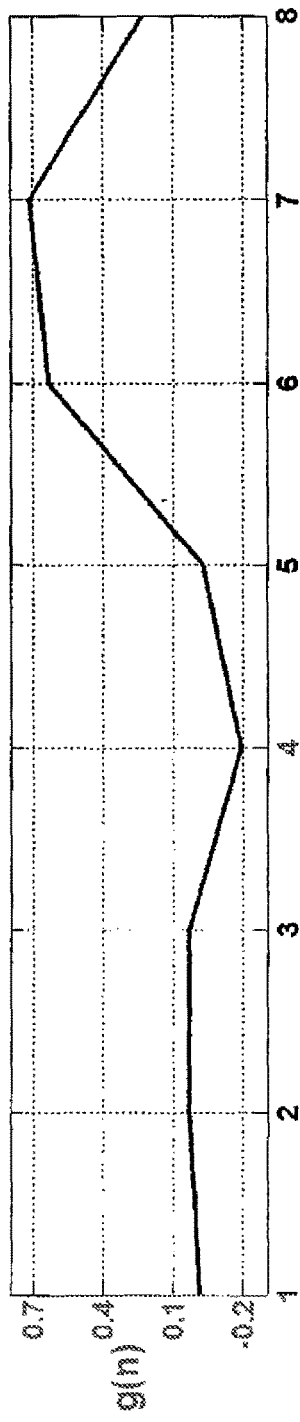
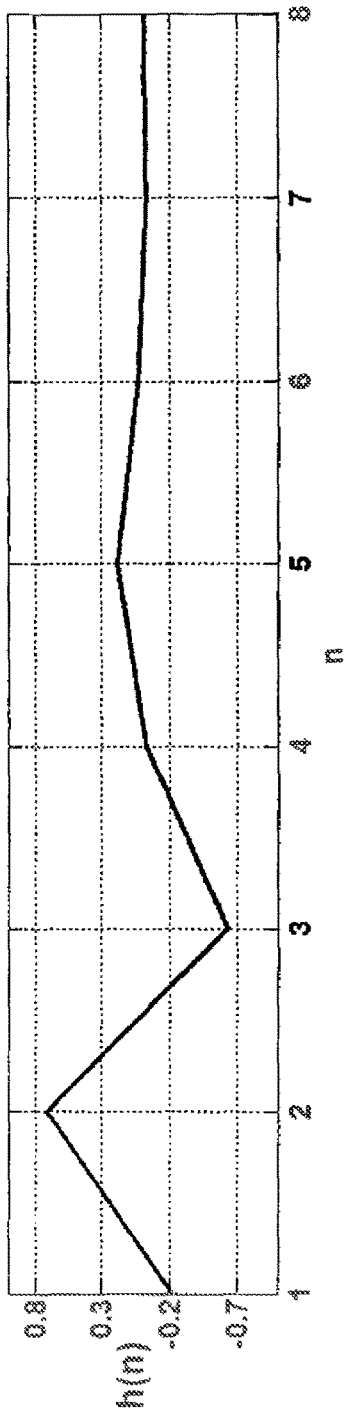

METHOD, NON-TRANSITORY COMPUTER READABLE MEDIUM AND APPARATUS FOR AROUSAL INTENSITY SCORING

CROSS-REFERENCE TO RELATED APPLICATION

This application claims the benefit of U.S. Provisional Application No. 61/859,905 filed on Jul. 30, 2013, the entire content of which is incorporated herein by reference.

FIELD

The subject disclosure relates to a method, non-transitory computer readable medium and apparatus for arousal intensity scoring.

BACKGROUND

Poor sleep quality is rapidly being recognized as a major health problem in that it results in non-restorative sleep with daytime fatigue, decreased cognitive function, excessive daytime sleepiness and increased risk of industrial, driving and recreational accidents. In addition, it is now becoming clear that poor sleep is a risk factor for development of hypertension (and its cardiovascular complications), as well as for the development of diabetes and depression and, possibly also, cognitive disorders such as Alzheimer's disease and other types of dementia.

The most reliable method of evaluating sleep quality is to conduct a sleep study in a specialized laboratory or in the home where electrodes are attached to the head of a subject to monitor the subject's brain activity (i.e. the electroencephalography (EEG) signal). The EEG signal is then analyzed either manually by a trained technologist or by an automated system. Sleep quality is evaluated by a number of parameters derived primarily from the EEG signal, and to a lesser extent from other recorded signals such as changes in heart rate, muscle tone and breathing. The parameters used clinically to evaluate sleep quality include total sleep time, sleep efficiency, times in different sleep stages, and importantly the frequency of arousals.

Arousals are temporary changes in the sleeping EEG signal pattern towards an awake EEG signal pattern. The standard definition of arousal by the American Academy of Sleep Medicine (AASM) is "an abrupt shift in EEG to a higher frequency, including alpha, theta or beta, for at least 3 seconds, with at least 10 seconds of stable sleep preceding the change" (Iber C. et al. *The AASM Manual for the Scoring of Sleep and Associated Events*. American Academy of Sleep Medicine, Westchester, Ill., 2007). However, EEG signal changes that meet this definition cover a very wide range of visual appearances, ranging from changes that barely meet the scoring criteria to very intense changes associated with very high amplitude beta waves. FIG. 1 shows examples of EEG signals comprising arousals that differ greatly in their visual intensity. In panels A to D of FIG. 1, an arousal begins near the middle of each EEG signal. In panel A, the increase in EEG signal frequency is subtle while in panel D the change in visual appearance of the EEG signal is quite gross, with intermediate changes in the visual appearance of the EEG signals being shown in middle panels B and C. In the current state of the art, arousals, whether scored manually or by an automated system, are treated equally. They are simply counted without any regard to their intensity.

There is evidence that the visual intensity of arousals is correlated with the magnitude of physiological changes that accompany arousals. Thus, Younes reported that the visual intensity of arousals (classified into four (4) levels) correlated with the magnitude of the ventilatory overshoot that follows obstructive events in obstructive sleep apnea patients (*Role of arousals in the pathogenesis of obstructive sleep apnea. Am J Respir Crit Care Med* 2004; 169:623-33). Also, Sforza et al. found that heart rate increased more in arousals associated with movement (*Cardiac activation during arousal in humans: further evidence for hierarchy in the arousal response. Clinical Neurophysiology* 2000; 111: 1611-9). Thus, it is possible that scoring the intensity of arousals may provide additional guidance into which patients with sleep disorders will develop cognitive and/or cardiovascular complications.

As will be appreciated, visual scoring of arousal intensity to assign values to arousals within a scale is very time consuming and, because of its subjective nature, prone to much inter-scorer variability. In order to test the clinical significance of arousal intensity in an efficient and accurate manner, a need exists to improve arousal intensity scoring. It is therefore an object to provide a novel method, non-transitory computer readable medium and apparatus for arousal intensity scoring.

SUMMARY

Accordingly, in one aspect there is provided a computerized method comprising: statistically analyzing, using one or more processors, at least one section of a digitally recorded electroencephalography (EEG) signal that comprises an arousal segment to determine, for the arousal segment, at least one of amplitude and power at different frequencies as a function of time; selecting specified features from the results of said analysis and normalizing the selected features; and assigning, using one or more processors, an intensity scale value to the arousal segment based on the normalized selected features and a reference data set, said reference data set comprising normalized features corresponding to the normalized selected features and being generated based on a plurality of EEG signals comprising arousal segments to which intensity scale values have been assigned based on a visual inspection of the EEG signals.

According to another aspect there is provided a non-transitory computer-readable medium embodying a computer program comprising instructions, which when executed by one or more processors, cause an apparatus at least to: statistically analyze at least one section of a digitally recorded electroencephalography (EEG) signal that comprises an arousal segment to determine, for the arousal segment, at least one of amplitude and power at different frequencies as a function of time; select specified features from the results of said analysis and normalize the selected features; and assign an intensity scale value to the arousal segment based on the normalized selected features and a reference data set, said reference data set comprising normalized features corresponding to the normalized selected features and being generated based on a plurality of EEG signals comprising arousal segments to which intensity scale values have been assigned based on a visual inspection of the EEG signals.

According to another aspect there is provided an apparatus comprising: memory; and one or more processors operatively associated with said memory and configured to execute program instructions in said memory to cause said apparatus at least to: statistically analyze at least one section of at least one digitally recorded electroencephalography (EEG) signal stored in said memory that comprises an arousal segment to determine, for the arousal segment, at least one of amplitude and power at different frequencies as a function of time; select specified features from the results of said analysis and normalize the selected features; and assign an intensity scale value to the arousal segment based on the normalized selected features and a reference data set, said reference data set comprising normalized features corresponding to the normalized selected features and being generated based on a plurality of EEG signals comprising arousal segments to which intensity scale values have been assigned based on a visual inspection of the EEG signals.

BRIEF DESCRIPTION OF THE DRAWINGS

Embodiments will now be described by way of example only with reference to the accompanying drawings in which:

FIG. 8 shows wavelet and scaling filters;

DETAILED DESCRIPTION OF EMBODIMENTS

Figure 1:
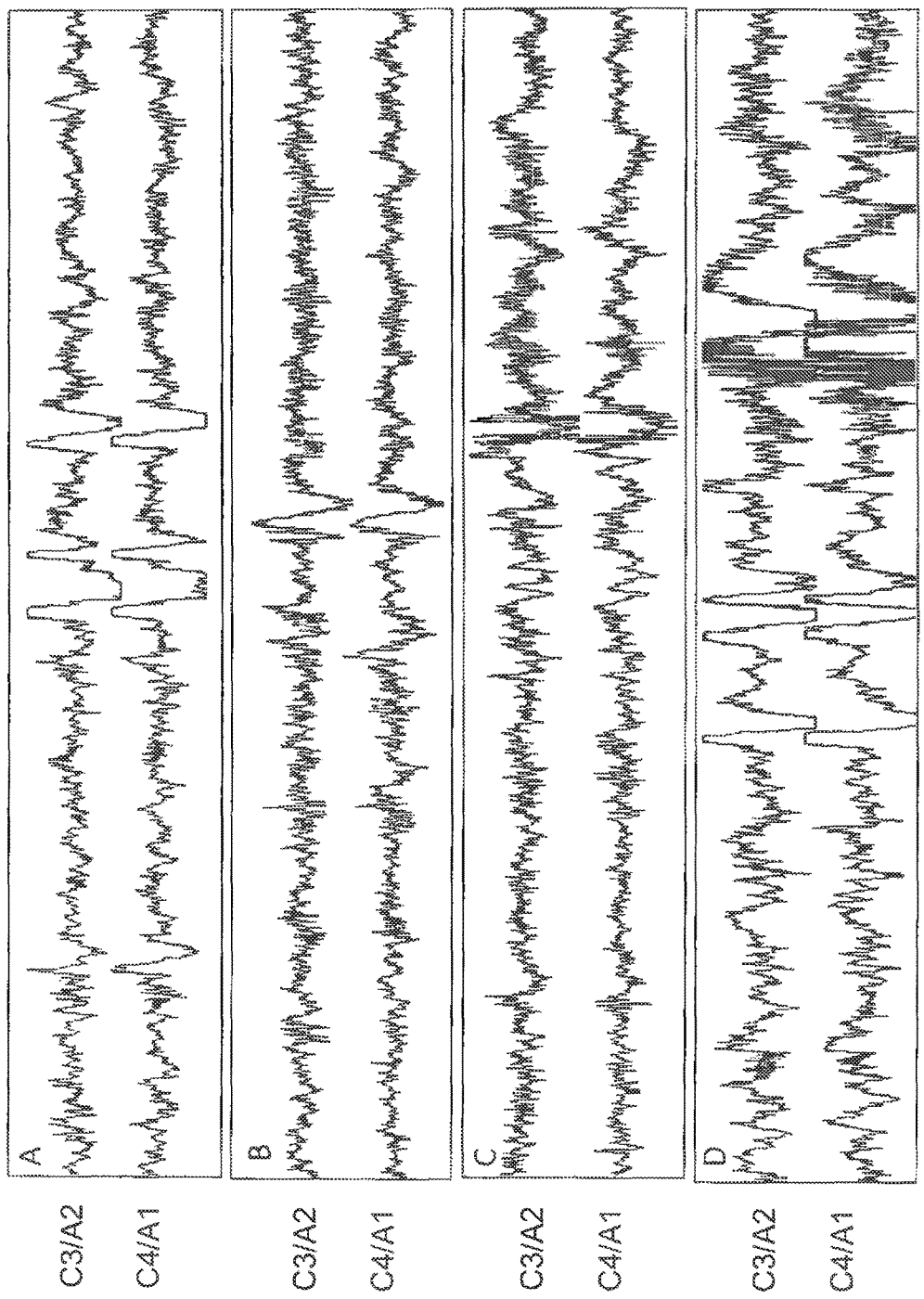
FIG. 1 shows examples of EEG signals comprising arousals that differ greatly in visual appearance.

In the subject application, a method for the automatic scoring of arousal intensity after the presence (i.e. yes/no) of arousals in an EEG signal has been identified through standard manual or automatic scoring is disclosed. When employed in an apparatus, the method can be used to assign an arousal intensity scale value to each identified arousal. The assigned intensity scale values of all arousals in the EEG signal may then be subjected to statistical analysis, the nature of which can be customized to the preference of care givers/investigators. Examples may include overall average arousal intensity, intensity in different sleep stages, intensity at different times in the sleep study . . . etc. In addition, it has been found that the heart rate response to a given arousal intensity varies considerably among patients and it is believed that the relation between arousal intensity and heart rate (HR) response will identify individuals who are at risk of developing cardiovascular complications from sleep fragmentation (Azarbarzin et al. *Relationship between Arousal Intensity and Heart Rate Response to Arousal. Sleep* 2014; 37:645-53). When combined with measurement of heart rate increase following arousal, the subject method can provide an index of the HR arousal intensity relation, such as the slope of the relation or the increase at specified arousal intensities. This index would be quite useful in epidemiological studies that evaluate the risk of cardiovascular complications in sleep disorders or the impact of medications on this response, and can be incorporated subsequently in clinical sleep reports.

In general, during the method segments of the EEG signal that contain arousals and their onset and end times are identified. For each identified arousal segment, an associated baseline segment of suitable duration is identified. The baseline segment may be of a duration equal to the duration of the arousal segment. Alternatively, the baseline segment may be a three (3) minute period of the EEG signal containing the arousal segment. Of course, those of skill in the art will appreciate that alternative baseline segments thr the arousal segments may be identified. Clearly, the duration and location of the baseline segments relative to the arousal segments can vary.

Statistical analysis of each baseline and arousal segment pair is then performed. The general intent of this statistical analysis is to calculate amplitude and/or power in selected frequencies or frequency ranges over specified time intervals. A number of standard methods are available to obtain this information including but not limited to Gabor Transform (Short Time Fourier Transform), Wavelet Transform, Empirical Mode Decomposition (EMD) or High Order Statistics (HOS) (Boashash B. *Time Frequency Signal Analysis and Processing: a comprehensive reference*, Elsevier 2003, Kidlington, Oxford; Cohen L. *Time-Frequency Analysis*, Prentice Hall PTR 1995, New Jersey).

For example, wavelet transform may be used to identify a number of features of each arousal segment, known from studies on a large number of arousals, that correlate with visually identified arousal intensity (Azarbarzin et al. *Relationship between Arousal Intensity and Heart Rate Response to Arousal. Sleep* 2014; 37:645-53). Alternatively, the power in different frequency ranges of the EEG signal in consecutive three (3) second intervals may be calculated using Fast Fourier Transform. In this case, the frequency ranges used are the standard delta (0.5-2.5 Hz), theta (2.5-7.0 Hz), alpha/signal (7.0-14.0 Hz) and beta (14.0-35.0 Hz). In addition, the high-pass filtered heart rate, respiratory amplitude and chin EMG amplitude during and following each arousal segment may be calculated.

The relative change in selected identified features associated with each arousal segment is then calculated. This is a normalization procedure that can be implemented in any number of ways. For example, the ratio of the value during the arousal segment of each selected feature to its value during the baseline segment may be calculated. Alternatively, the ratio of power in each EEG frequency band, or the value of other ancillary signals (i.e. filtered heart rate, respiratory amplitude or chin EMG amplitude), obtained during each three (3) second interval to the $70^{th}$ percentile of all values in a three (3) minute time block containing the arousal segment may be calculated.

An arousal intensity scale value is then assigned to each identified arousal segment using the normalized features. This step utilizes a training data set. The training data set may be in the form of a reference table containing the values of the features being utilized that are associated with a suitable number of arousals (two-hundred and seventy-one (271) in one embodiment as will be described) whose intensities were visually determined by an expert scorer or a group of expert scorers. The process of matching the features of an identified arousal segment to the appropriate arousal intensity scale value in the training data set may take any of a number of standard forms. For example, the wavelet transform may be used to analyze the arousals used to construct the training data set (reference arousals) in the same way as the identified arousal segments, that is determining the relevant wavelet features during and preceding the reference arousals and the ratio of the two values. Because the number of arousal intensities is limited (0 to 9, or 10 intensities, in this case), there are many arousals at each arousal intensity level in the training data set (about twenty-seven (27) on average in one embodiment as will be described). Thus, there are many feature combinations that can be associated with each visually determined arousal intensity. To select the most appropriate arousal intensity scale value for a given arousal segment, a number of standard classifiers are used.

Alternatively, the selected features are made up of the ratios of the powers in different frequency ranges (e.g. beta power during arousal/$70^{th}$ percentile of beta powers in the preceding three (3) minutes . . . etc) and/or combinations of these ratios (products). For example, one product consists of five (5) ratios multiplied by each other (e.g. alpha ratio*beta ratio*chin EMG ratio*heart rate ratio*respiratory amplitude ratio). Another product consists of the product of alpha and beta ratios only, thereby describing the relative change in high frequency power. Yet another product describes the change in ancillary features alone (chin EMG ratio*heart rate ratio*respiratory amplitude ratio). Any number of combinations can be utilized. These products are also calculated for the reference arousals in the training data set. The features calculated for an identified arousal segment are assigned an arousal intensity scale value by reference to the training data set. Matching is accomplished by use of classifiers, or by use of a formula developed from the relation between visually-sealed arousals and one or more of the features associated with them in the training data set.

Figure 2:
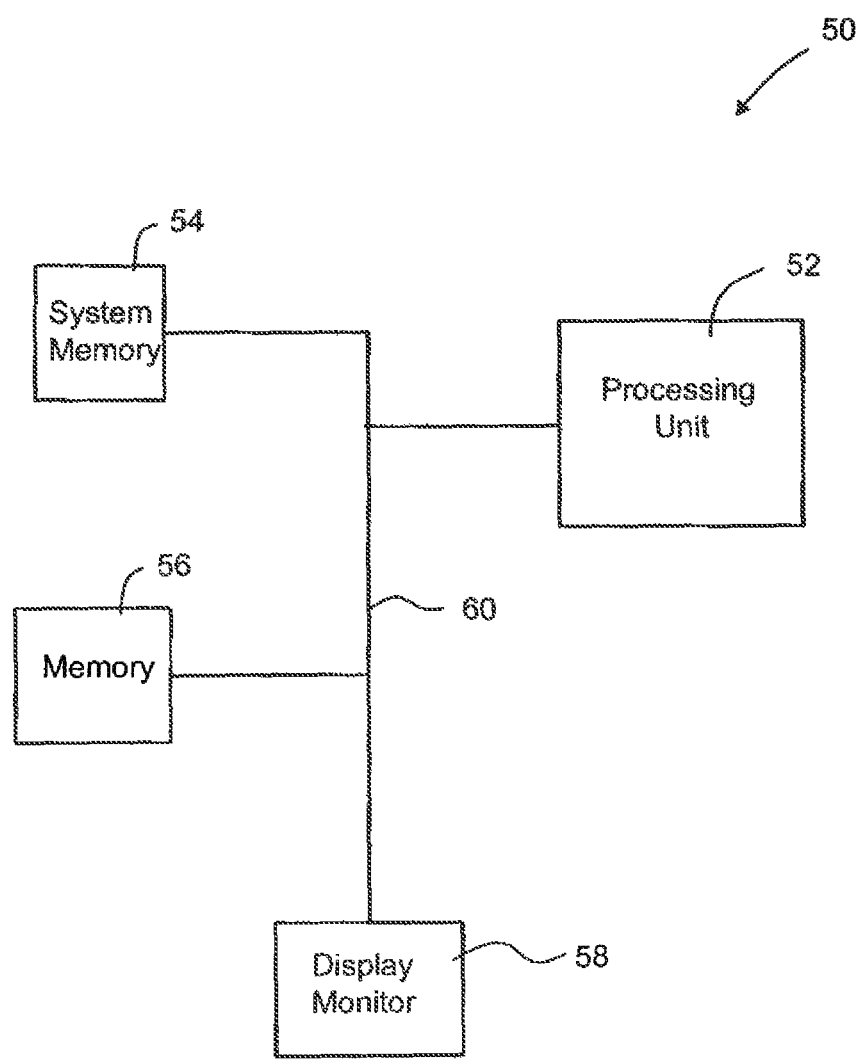
FIG. 2 is a schematic block diagram of an apparatus in the form of a general purpose computing device for arousal intensity scoring.

Turning now to FIG. 2, an apparatus for arousal intensity scoring is shown and is generally identified by reference numeral 50. In this embodiment, the apparatus 50 is in the form of a general purpose computing device such as a personal computer or other suitable processing device. The general purpose computing device comprises, for example, a processing unit 52 comprising one or more processors, system memory 54 (volatile and/or non-volatile memory), other non-removable or removable memory 56 (e.g., a hard disk drive, RAM, ROM, EEPROM, CD-ROM, DVD, flash memory, etc.), a display monitor or screen 58 and a system bus 60 coupling the various computing device components to the processing unit 52. The memory 56 stores one or more digital EEG files recorded during a sleep study or during another sleep event that are to be processed in order to evaluate arousal intensity. Each EEG file comprises arousal segments and has preferably been pre-scored so that the onset time and end time of each arousal segment is identified. As will be appreciated, the identified onset and end time of each arousal segment may represent the true onset and end times of the arousal segment or may represent some other period containing part or all of the arousal segment. The memory also stores an arousal intensity scoring program or application that is executed by the processing unit 52 in order to process the EEG files as will be described. The general purpose computing device may also comprise networking capabilities using Ethernet, WiFi, and/or other suitable network format, to enable connection to shared or remote drives, one or more networked computers, or other networked devices. The general purpose computing device may optionally comprise one or more other input devices such as a mouse, keyboard, trackball etc.

Figure 3:
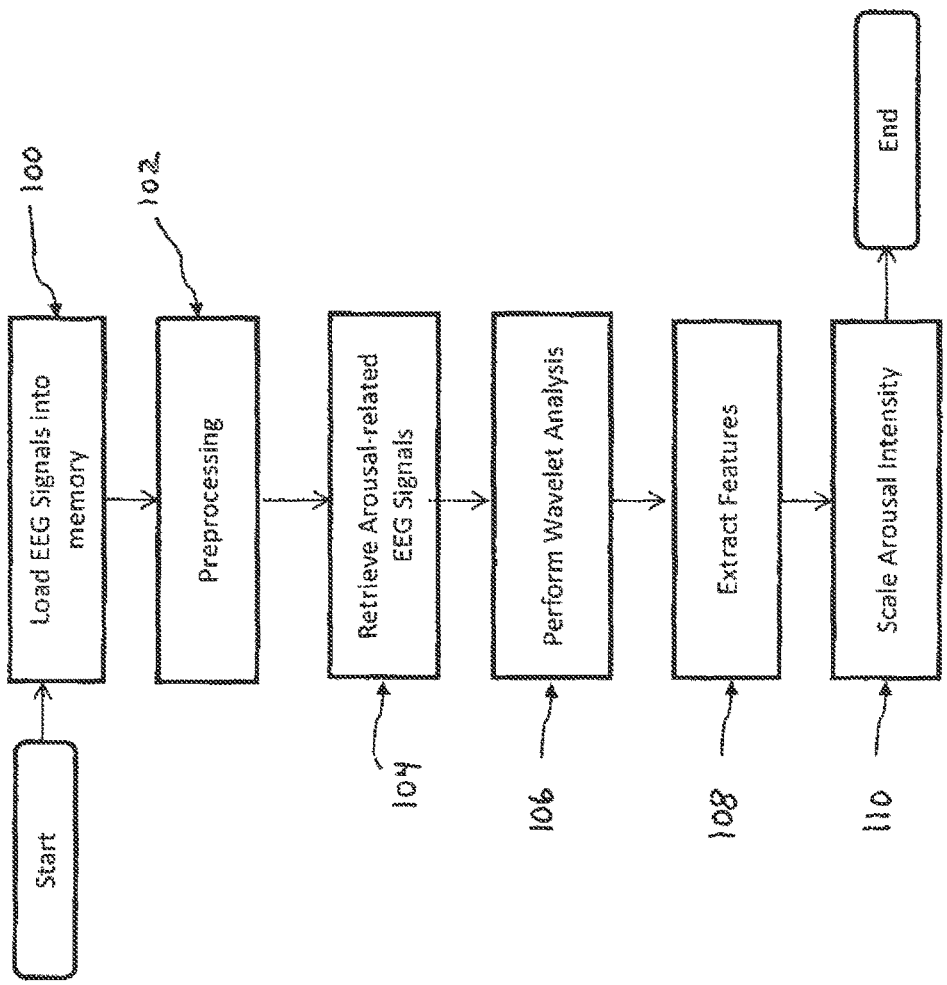
FIG. 3 is a flowchart showing an arousal intensity scoring methodology.

FIG. 3 shows the steps performed by the apparatus 50 during execution of the arousal intensity scoring program. Initially, an EEG file in the memory 56 that is to be analyzed is selected (step 100). Once selected, the EEG file is preprocessed (step 102) in which the entire EEG file is filtered. Following step 102, sections of the EEG file that comprise an arousal segment and an associated baseline segment of at least similar duration preceding the arousal segment are retrieved from the EEG file (step 104). One of the retrieved EEG file sections is then selected and a wavelet transform on the arousal segment and baseline segment of the selected EEG file section is then performed (step 106). The relevant wavelet features are then extracted (step 108) and an intensity scale value is assigned to the arousal segment (step 110) by reference to a training data set. A check is then performed determine if one or more retrieved EEG file sections that have not been selected exist. Steps 106 to 110 are repeated for each retrieved EEG file section until all retrieved EEG file sections have been processed.

As will be appreciated, once all of the retrieved EEG file sections have been processed, an arousal intensity scale value for each of the arousal segments in the EEG file exists. The arousal linens scale values and the EEG file are then combined and saved as a digital file in memory 56. The arousal intensity scale values can be presented on the display monitor 58, transmitted electronically and/or printed with or without the associated EEG file sections. The results of the arousal intensity scoring in the digital file can then be reported in either digital or paper form, alone or as part of a more comprehensive report that describes other findings from the sleep study. The arousal intensity scoring can then be used by physicians or investigators as a measure of the extent of sleep fragmentation caused by electro-cortical arousals. As mentioned earlier, the arousal intensity scale values may be subjected to statistical analysis to determine, for example, overall average arousal intensity, intensity in different sleep stages, intensity at different times in the sleep study etc. and the arousal intensity scale values may be combined with other ancillary signals such as heart rate to identify individuals who are at risk of developing cardio-vascular complications or the impact of medications.

Figure 4:
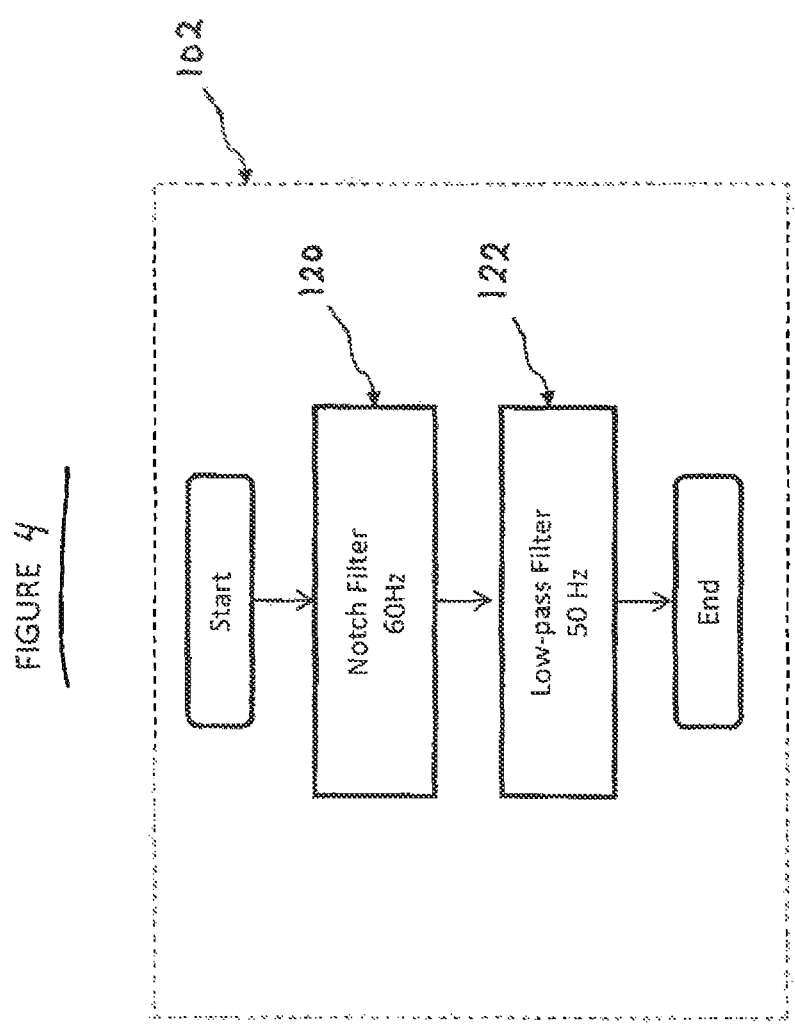
FIG. 4 is a flowchart showing the steps of a preprocessing stage forming part of the arousal intensity scoring methodology of FIG. 3.

FIG. 4 better illustrates the steps performed during pre-processing of the selected EEG file at step 102. Initially, the entire selected EEG file is filtered by a 60 Hz Notch filter (step 120). Thereafter, the entire selected EEG file is filtered by a $12^{th}$ order 50 Hz low pass filter (step 122).

Figure 5:
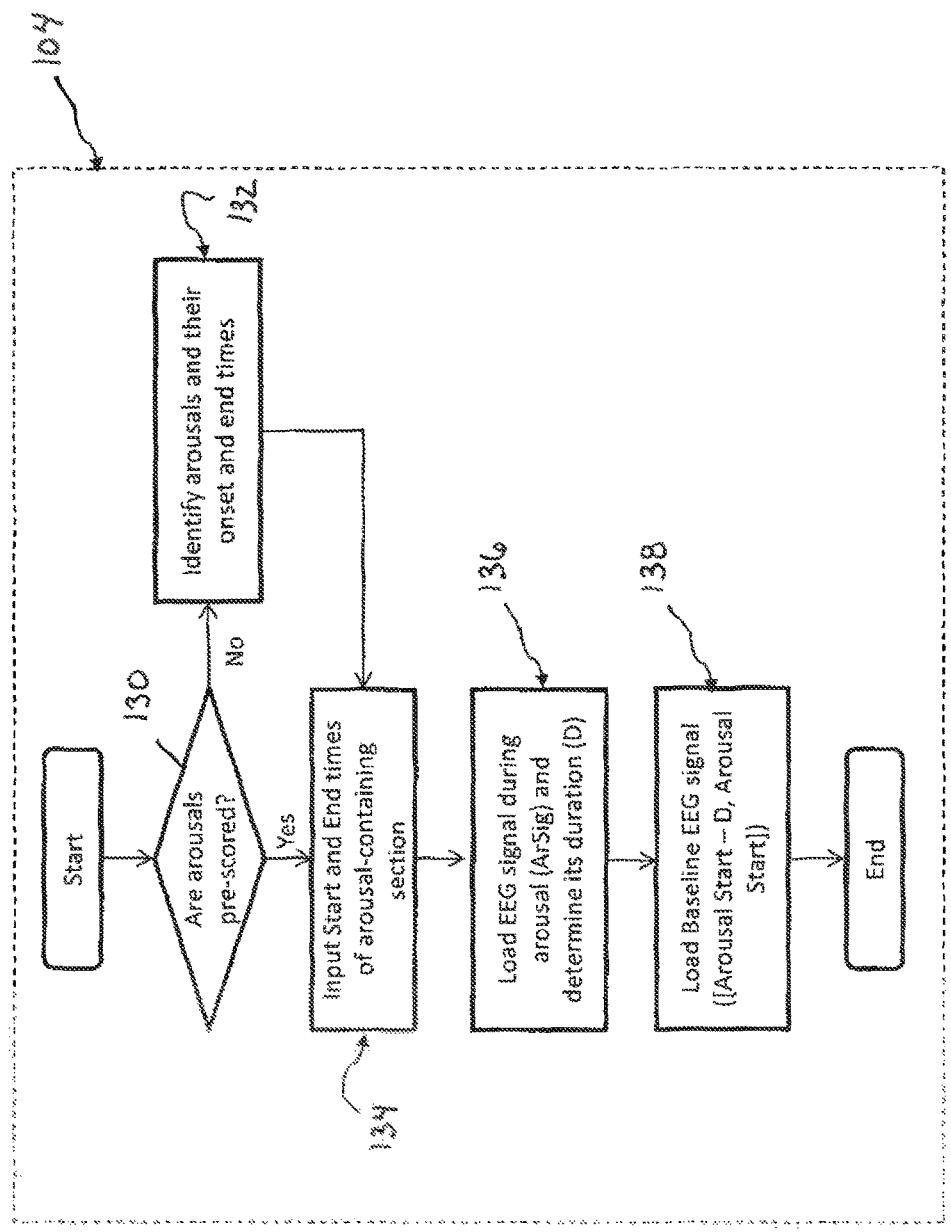
FIG. 5 is a flowchart showing the steps of a retrieve arousal related EEG signals stage forming part of the arousal intensity scoring methodology of FIG. 3.

FIG. 5 better illustrates the steps performed during retrieval of EEG file sections that comprise an arousal segment and a baseline segment at step 104. Initially, a check is made to determine if the arousals in the selected EEG file have been pre-scored to identify the onset time and end time of each arousal-containing EEG file section (step 130). If the arousals in the selected EEG file have not been pre-scored, the selected EEG file is scored to identify the onset time and end time of each arousal-containing EEG file section (step 132). Scoring of the arousal-containing EEG file sections may be performed manually or may be performed using an automated system that executes arousal intensity scoring software. If scoring of the arousal-containing EEG file sections is performed using an automated system, the scoring results may be manually edited. In this embodiment, the Michele Sleep Scoring System (Younes Sleep Technologies of Winnipeg, Manitoba) is employed to score automatically the selected EEG file followed by manual editing. At step 130, if the arousals in the selected EEG file have been pre-scored or following scoring of the arousals in the selected EEG file at step 132, the onset time and end time of each arousal-containing EEG file section is determined (step 134). For each arousal-containing EEG file section, the EEG signal between the onset time and end time, i.e. the arousal segment (ArSig), is identified and the duration (D) of the arousal segment is calculated by subtracting the end time from the onset time (step 136). Next, a segment of the EEG signal that precedes the onset time of the identified arousal segment and that has the same or substantially the same duration as the identified arousal segment, i.e. the baseline segment, is identified (step 138) thereby to yield the arousal and baseline segment pair of the arousal-containing EEG file section.

Figure 6:
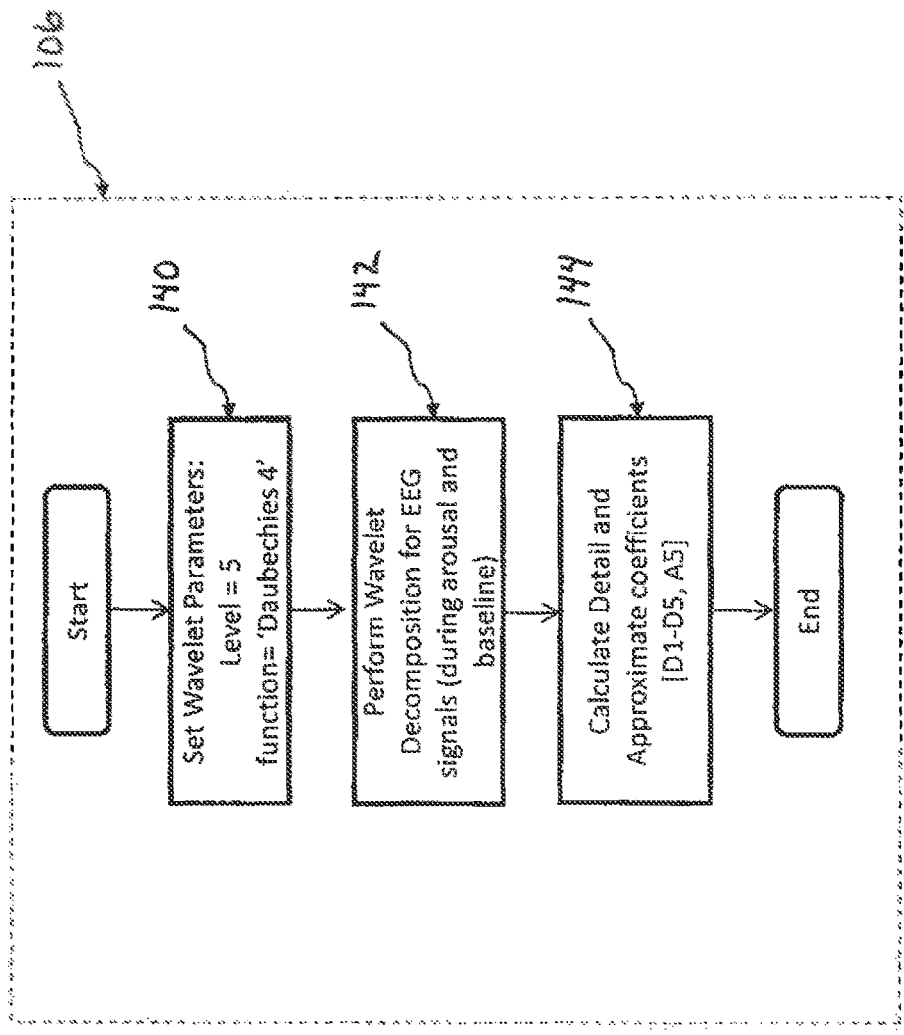
FIG. 6 is a flowchart showing the steps of a wavelet analysis stage forming part of the arousal intensity scoring methodology of FIG. 3.
Figure 7:
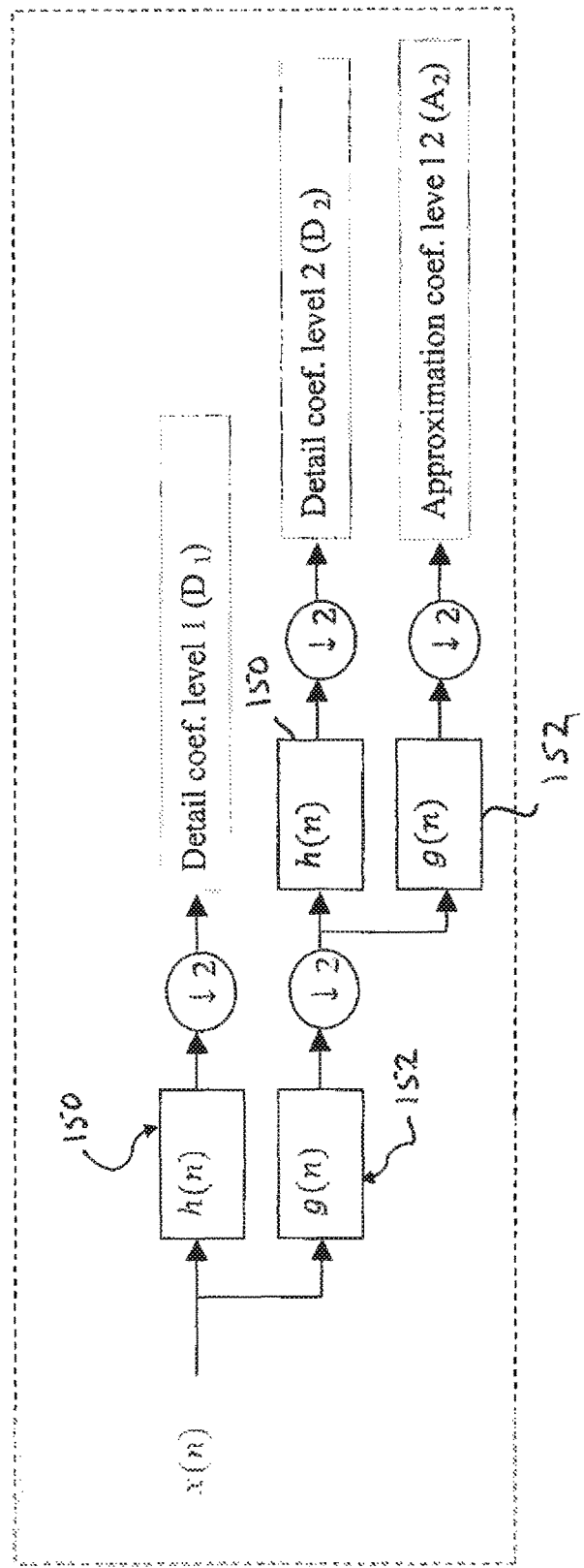
FIG. 7 is a schematic diagram showing two (2) level wavelet decomposition of a signal using discrete wavelet transform.

FIG. 6 better illustrates the steps performed during wavelet analysis of each EEG file section that comprises an arousal segment and a baseline segment at step 106. Initially, the parameters of the wavelet transform are set (step 140). Although several wavelet transforms have been proposed in the literature, in this embodiment, a Daubechies wavelet of order four (4), level five (5) is used (Daubechies I. *Orthonormal bases of compactly supported wavelets. Communications on Pure and Applied Mathematics* 1988; 41:909-96). Those of skill in the art will appreciate that Daubechies wavelets are known for their orthogonality and efficient implementation and their order four (4) has been found to be effective for the analysis of EEG signals (Adeli H, et al. *Analysis of EEG records in an epileptic patient using wavelet transform. J Neurosci Methods* 2003; 123:69-87). Since the signal of each EEG file section is discrete, discrete wavelet transform (DWT) is used, which is obtained by taking the wavelet and scaling functions at discrete values. For illustrative purposes, a simple two (2) level wavelet decomposition of a signal using DWT is shown in FIG. 7.

Following step 140, the wavelet transform by Daubechies wavelet, order four (4), with five (5) levels is performed on both the arousal and baseline segments of the EEG file section (step 142). Calculating the Daubechies wavelet is performed using standard signal analysis techniques that are well known to those of skill in the art and described in the literature (see above references) and therefore, details of these calculations will not be repeated herein. Briefly however, the DWT of the arousal and baseline segments of the EEG file section is calculated by passing the arousal and baseline segments of the EEG file section through a series of cascade filters. As shown in FIG. 7, in each level of decomposition, the arousal and baseline segments of the EEG file section (or the approximation coefficients) are passed through two special filters, namely a high pass (or wavelet) filter (h(n)) (150) and a low pass (or scaling) filter (g(n)) (152). FIG. 8 shows the wavelet and scaling filters for Daubechies wavelet order four (4). The high pass and low pass filters 150 and 152, respectively, are related to each other and they are quadrature mirror filters. The frequency ranges corresponding to different levels of decomposition depend on the number of levels and sampling frequency.

Following wavelet decomposition at step 142, the detail and approximation coefficients (D1 to D5 and A5) are calculated for the arousal and baseline segments of the EEG file section (step 144). Table 1 below shows the frequency range of the detail and approximation coefficients for the five (5) levels of decomposition at a sampling frequency of 128 Hz.

TABLE 1

Frequency ranges corresponding to 5 levels of decomposition using Daubechies wavelet order 4

| Coefficients | $D_1$ | $D_2$ | $D_3$ | $D_4$ | $D_5$ | $A_5$ |
|---|---|---|---|---|---|---|
| Frequency range (Hz) | 32-64 | 16-32 | 8-16 | 4-8 | 2-4 | 0-2* |

Figure 9:
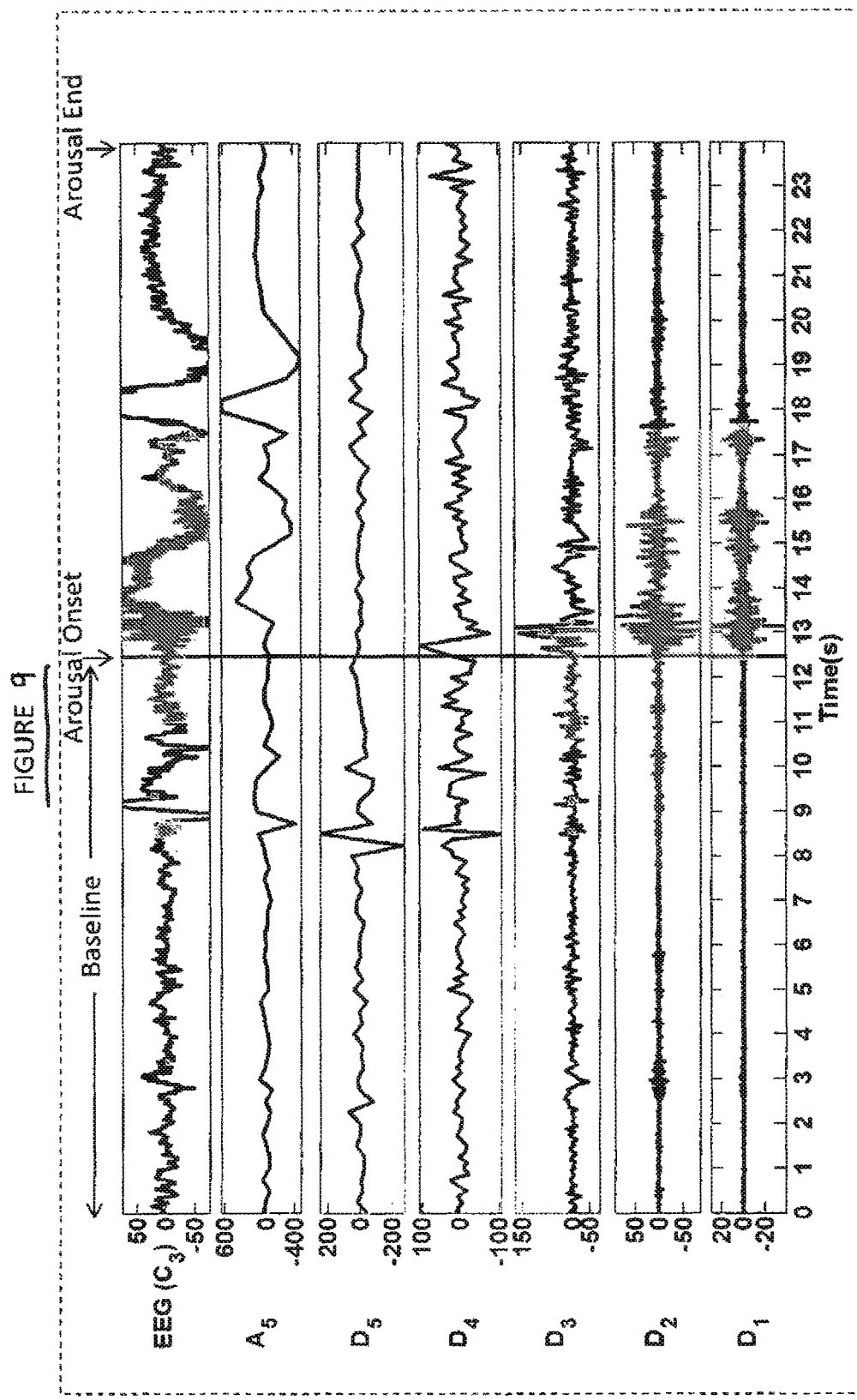
FIG. 9 shows an EEG file section comprising baseline and arousal segments together with detail and approximation coefficients calculated for the baseline and arousal segments.

The original EEG signal was passed through a high pass filter with a cut-off frequency of 0.3 Hz FIG. 9 shows baseline and arousal segments of an EEG file section together with detail and approximation coefficients calculated for the baseline and arousal segments.

Figure 10:
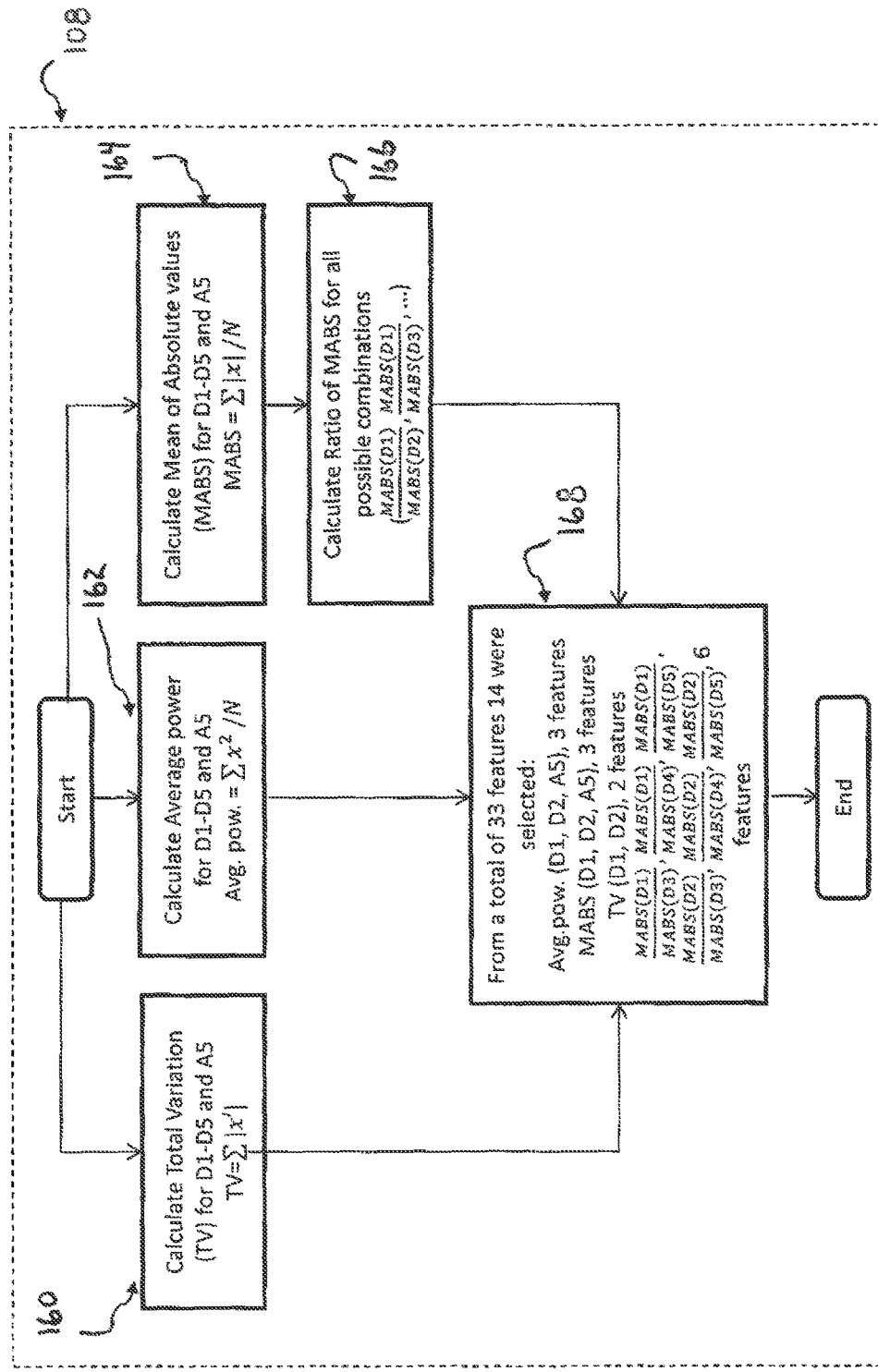
FIG. 10 is a flowchart showing the steps of a feature extraction stage forming part of the arousal intensity scoring methodology of FIG. 3.

FIG. 10 better illustrates the steps performed during feature extraction at step 108. As will be appreciated by those of skill in the art, a large number of features can be extracted from the wavelet coefficients and the choice of extracted features is user selectable. In this embodiment, the following features are calculated separately for the baseline and arousal segments of each EEG file section:

Total variation for the detail coefficients D1 to D5 and the approximation coefficient A5 (step 160). This is the sum of absolute sample to sample change in each coefficient within the period being analyzed (i.e. the arousal and baseline segment durations) and results in a maximum of six (6) features extracted over the arousal segment and a maximum of six (6) features extracted over the baseline segment.

Average power for the detail coefficients D1 to D5 and the approximation coefficient A5 (step 162). This is the sum of squares of all samples within the period being analyzed divided by number of samples and results in a maximum of six (6) features extracted over the arousal segment and a maximum of six (6) features extracted over the baseline segment.

Mean of absolute values (MABS) of the detail coefficients D1 to D5 and the approximation coefficient A5 (step 164). This is the sum of absolute values of all samples within the period being analyzed divided by the number of samples and results in a maximum of six (6) features extracted over the arousal segment and a maximum of six (6) features extracted over the baseline segment.

Ratios of MABS (step 166). These are the ratios of each of the six (6) MABS to each of the other five (5) MABS (e.g. (MABS(D1))/(MABS(D2)), (MABS(D1))/(MABS(D3)), . . . etc). This results in fifteen (15) possible features extracted over the arousal segment and fifteen (15) possible features extracted over the baseline segment.

As will be appreciated, the above feature extraction process theoretically results in thirty-three (33) extracted features for the arousal segment and thirty-three (33) extracted features for the baseline segment of each EEG file section. It has been found by experimentation that only fourteen (14) features of the thirty-three (33) features referenced above correlate with visually scored arousal intensities. These fourteen (14) features comprise the average power for detail coefficients D1 and D2 and for approximation coefficient A5, MABS of the detail coefficients D1 and D2 and of approximation coefficient A5, the total variation for the detail coefficients D1 and D2 and the MABS ratios (MABS(D1))/(MABS(D3), (MABS(D1))/(MABS(D4), (MABS(D1))/(MABS(D5), (MABS(D2))/(MABS(D3), (MABS(D2))/(MABS(D4) and (MABS(D2))/(MABS(D5). Accordingly, in this embodiment only these fourteen (14) features are extracted (step 168). Those of skill in the art will however appreciate that features other than the features described above may be extracted. It will also be appreciated that visual scoring of arousal intensities by other scorers may result in different feature combinations being extracted.

Figure 11:
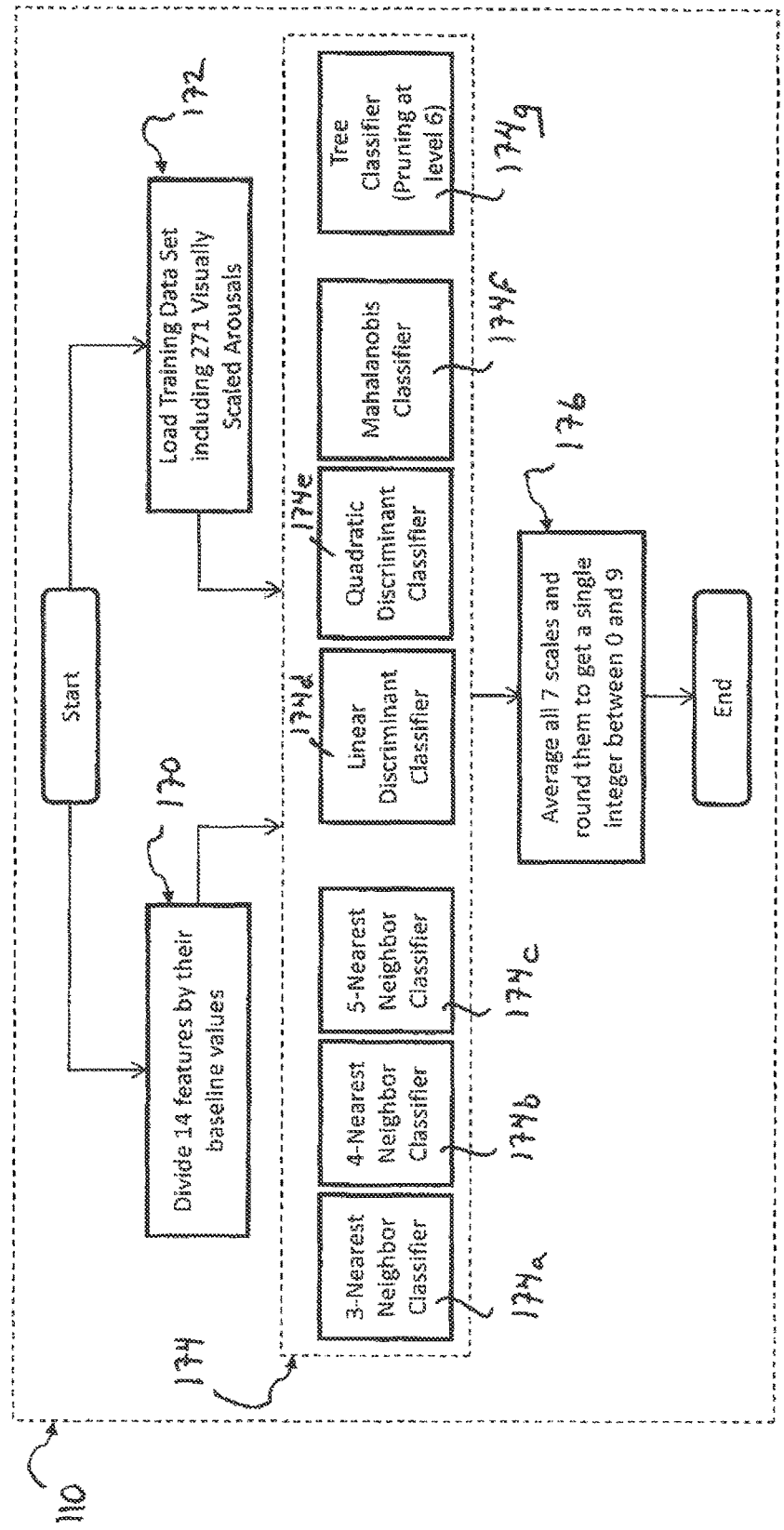
FIG. 11 is a flowchart showing the steps of an arousal intensity scaling stage forming part of the arousal intensity scoring methodology of FIG. 3.

FIG. 11 better illustrates the steps performed during arousal intensity scaling at step 110. Initially, each feature value extracted from the arousal segment is divided by the corresponding feature value extracted from the baseline segment to yield fourteen (14) feature ratios (step 170). The training data set which contains feature ratios is then loaded. The training data set in this embodiment was constructed following visual inspection by a scorer of two-hundred and seventy-one (271) arousals in three separate sleep EEG data files. An arousal intensity scale value was assigned to each arousal by the scorer, the arousal intensity scale value ranging from zero (0) to nine (9). The arousals were then subjected to the same process described above to generate fourteen (14) feature ratios of interest. The training data set therefore, consists of 271 rows each with one (1) column for the assigned arousal intensity scale value and fourteen (14) columns for the corresponding fourteen (14) feature ratios. As will be appreciated, since construction of the training data set is based on the visual inspection of EEG data files by a scorer, the training data set is clearly unique to the scorer. If desired, to avoid or minimize bias, training data sets can be constructed for other scorers or by consensus of a number of scorers.

Because the training data set contains many arousals with the same assigned arousal intensity scale value, with each arousal possibly associated with different feature ratios, assigning an arousal intensity scale value to an identified arousal segment requires a decision as to the arousal intensity scale value in the training data set that most agrees with the combination of feature ratios associated with the arousal segment. In this embodiment, this matching is accomplished by use of a number of standard classifiers (Duda R O, Hart P E, Stork D G. *Pattern classification: Wiley-Interscience*, 2000). In particular, seven classifiers generally identified by reference numeral 174 are used to classify each arousal segment based on the training data set. As can be seen, the seven classifiers comprise three k-nearest neighbor classifiers 174a to 174c (classifier 174a: k=3, classifier 174b: k=4, classifier 174c: k=5), three discriminant classifiers 174d to 174f (classifier 174d: linear discriminant, classifier 174e: quadratic discriminant, classifier 174f: Mahalanobis discriminant), and one tree classifier 174g with pruning at level six (6). Each classifier outputs an arousal intensity scale. The rounded average of the arousal intensity scales output by the seven classifier is then obtained (step 176) providing the final arousal intensity scale.

Figure 12:
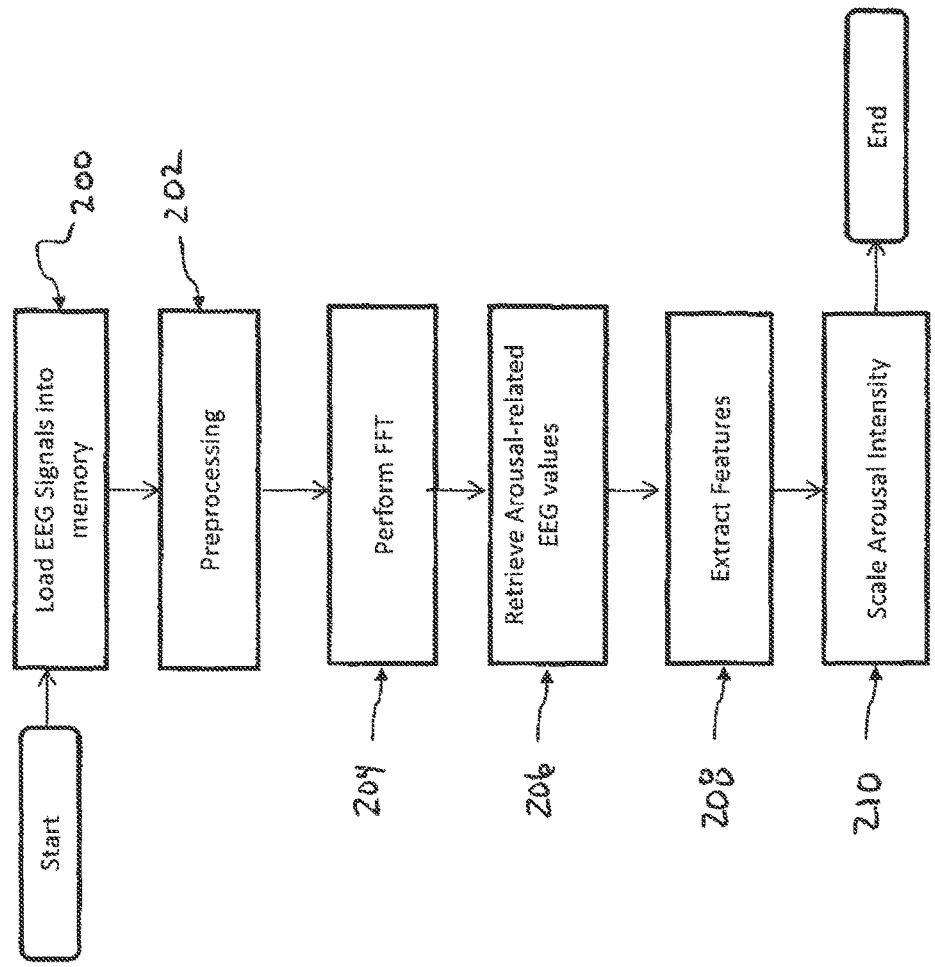
FIG. 12 is a flowchart showing an alternative arousal intensity scoring methodology.

FIG. 12 shows the steps performed by the apparatus 50 during execution of an alternative arousal scoring scaling program or application similar to that of the previous embodiment. Initially, an EEG file in the memory 56 that is to be analyzed is selected (step 200). Once selected, the EEG file is pre-processed (step 202) in which the entire EEG file is filtered. Following step 202, a Fast Fourier Transform is performed on the EEG file (step 204). Arousal related EEG values are then retrieved from the EEG file (step 206). Features are then extracted (step 208) and the arousal segments of the EEG file are assigned an arousal intensity scale value (step 210) using a training data set.

Figure 13:
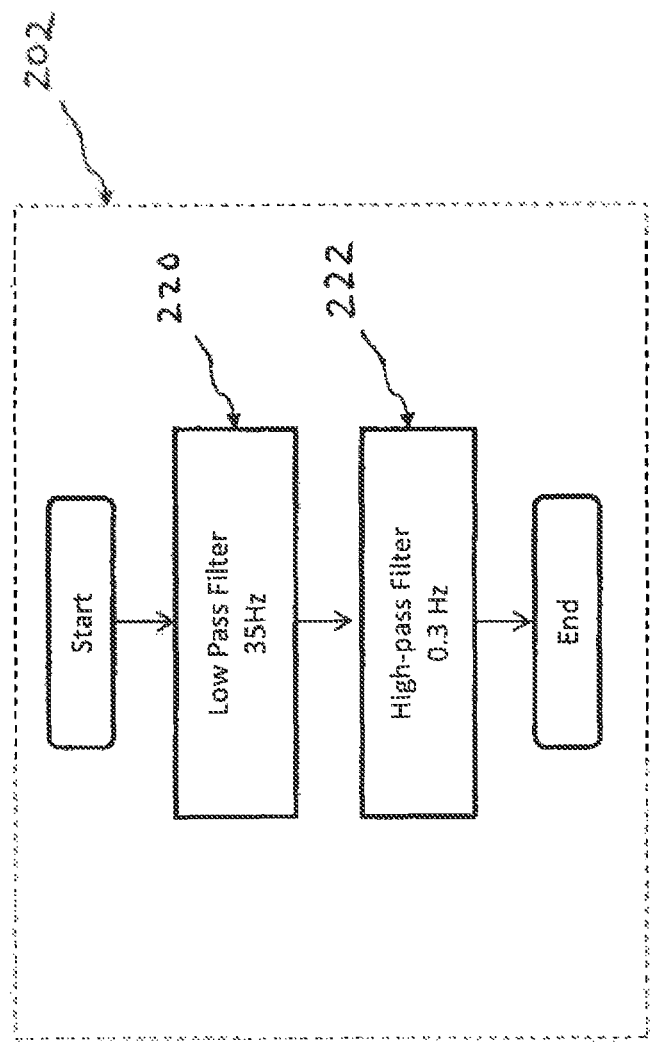
FIG. 13 is a flowchart showing the steps of a preprocessing stage forming part of the arousal intensity scoring methodology of FIG. 12.

FIG. 13 better illustrates the steps performed during pre-processing of the selected EEG file at step 202. In this embodiment, initially the entire selected EEG file is subjected to a 35 Hz low pass filter (step 220). Thereafter, the entire selected EEG file is subjected to a 0.3 Hz high pass filter (step 222).

Figure 14:
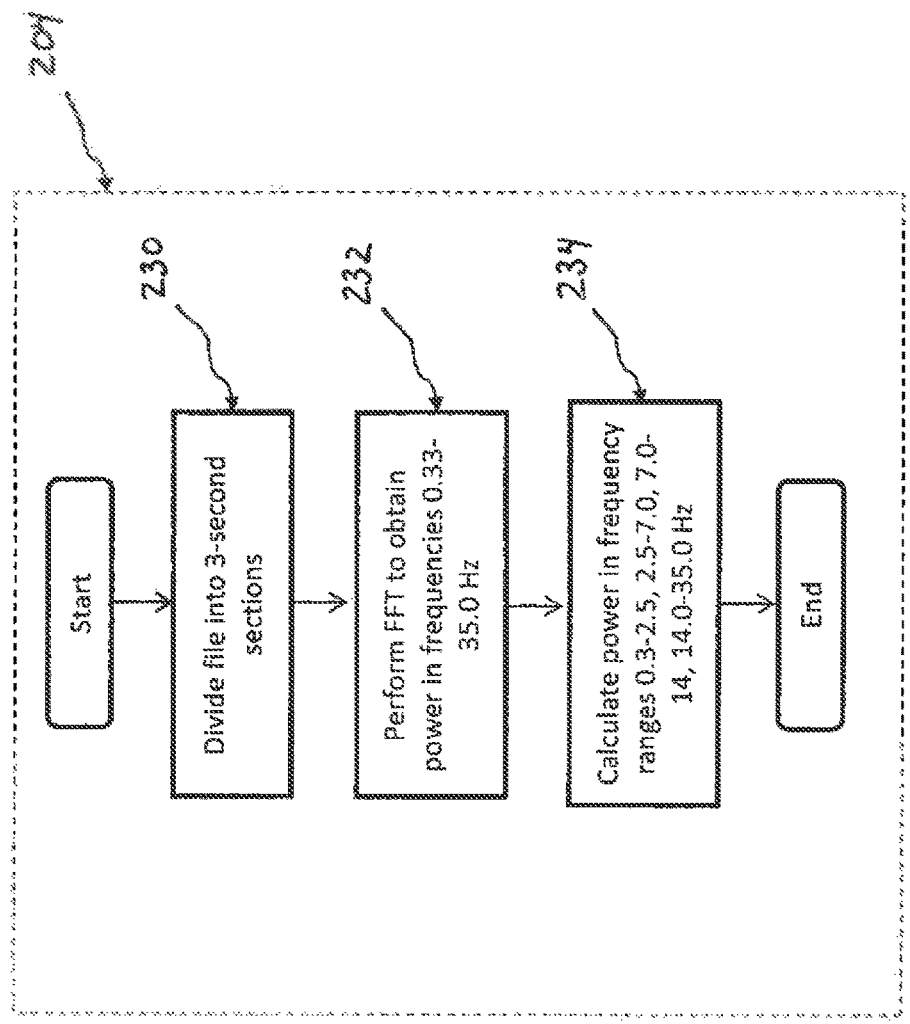
FIG. 14 is a flowchart showing the steps of a Fast Fourier Transform stage forming part of the arousal intensity scoring methodology of FIG. 12.

FIG. 14 better illustrates the steps performed during the Fast Fourier Transform stage at step 204. Initially, the selected EEG file is divided into consecutive intervals. In this embodiment, each interval has a three (3) second duration (step 230). The Fast Fourier Transform is then obtained on each three (3) second interval to provide the powers in the frequency range of 0.33-35.0 Hz (step 232). The sum of powers in four (4) selected frequency ranges is then calculated (step 234). These frequency ranges correspond to the standard delta range (0.5-2.5 Hz), theta range (2.5-7.0 Hz), alpha/sigma range (7.0-14.0 Hz) and beta range (14.0-35.0 Hz). Those of skill in the art will appreciate that the selected three (3) second duration for the consecutive intervals is not critical and that other interval durations may be employed.

Figure 15:
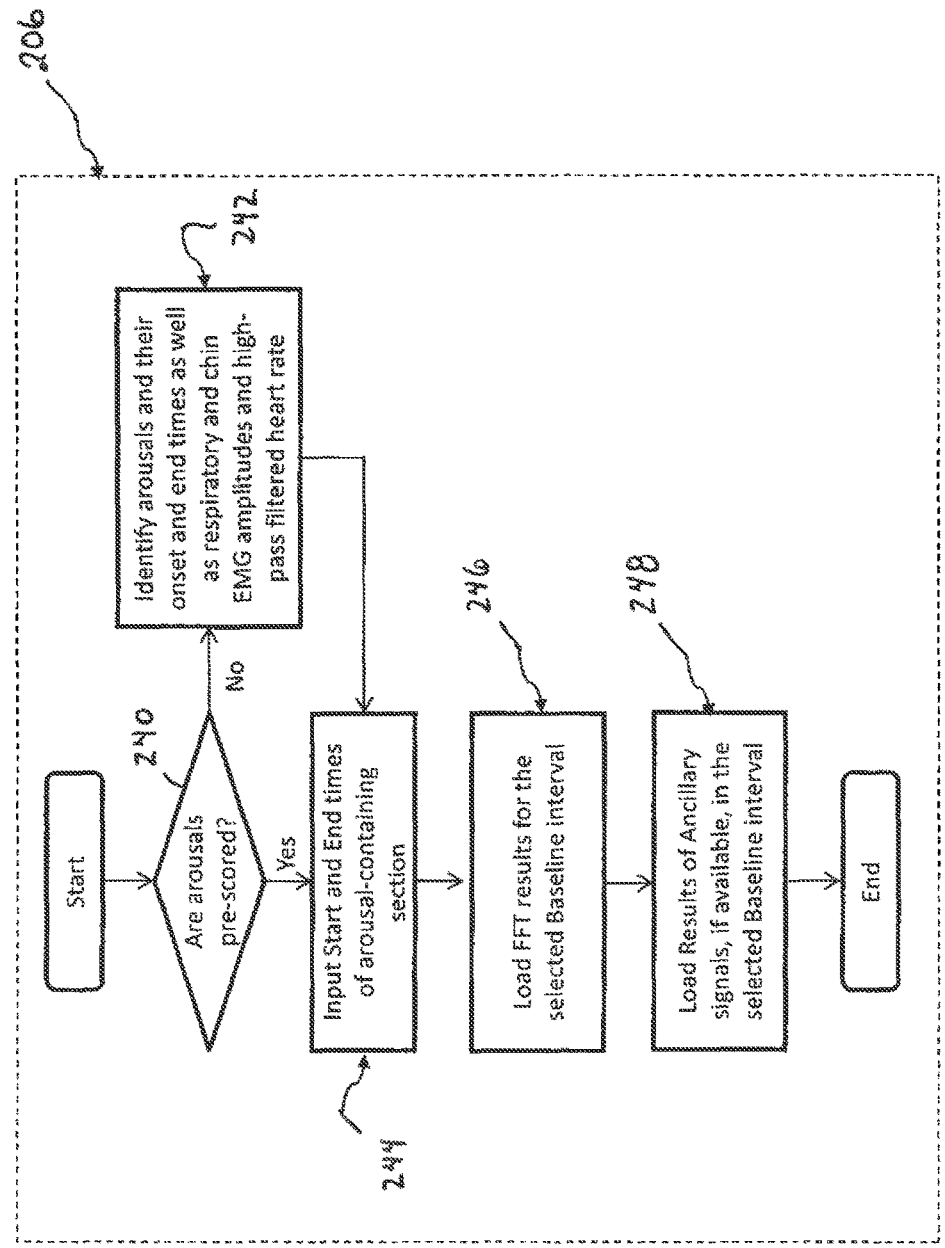
FIG. 15 is a flowchart showing the steps of a retrieve arousal related EEG signals stage forming part of the arousal intensity scoring methodology of FIG. 12.

FIG. 15 better illustrates the steps performed during retrieval of arousal related EEG values at step 206. Initially, a check is made to determine if the arousals in the selected EEG file have been pre-scored to identify the onset time and end time of each arousal-containing EEG file section (step 240). If the arousals in the selected EEG file have not been pre-scored, the selected EEG file is scored to identify the onset time and end time of each arousal-containing EEG file section together with ancillary signals such as respiratory and chin EMG amplitudes and high-pass filtered heart rate if they exist in the EEG file (step 242). As in the previous embodiment, scoring of the arousal-containing EEG file sections may be performed manually or may be performed using an automated system that executes arousal intensity scoring software. If scoring of the arousal-containing EEG file sections is performed using an automated system, the scoring results may be manually edited. In this embodiment, the Michele Sleep Scoring System (Younes Sleep Technologies) is employed to score automatically the selected EEG file followed by manual editing. At step 240, if the arousals in the selected EEG file have been pre-scored or following scoring of the arousals in the selected EEG file at step 242, the onset time and end time of each arousal-containing EEG file section is determined (step 244). Following step 244, for each arousal-containing EEG file section, the FFT results in a baseline interval containing the arousal segment are imported (step 246). In particular, the powers in the four frequency ranges for all three (3) second intervals contained in a three (3) minute baseline period are imported (i.e. sixty (60) sets of values). The interval used as the baseline is selected as follows. The onset and end of the sleep period in which the arousal segment occurred are identified. The sleep period is divided into three (3) minute intervals starting at the onset of the sleep period. The interval between the end of the sleep period and the end of the last complete three (3) second interval is measured (remaining interval). The remaining interval either constitutes a separate baseline period if it is greater than two (2) minutes or if it is less than or equal to two (2) minutes, it is absorbed in the preceding three (3) minute interval constituting a baseline period between three (3) and five (5) minutes. The interval to be used for the baseline is the interval containing the arousal segment, which may be two (2) to five (5) minutes in duration, but most commonly is three (3) minutes.

Sleep studies usually include monitoring of ancillary signals such as respiratory amplitude, heart rate and chin EMG amplitude. If these ancillary signals are available in the EEG file, they are imported at step (248).

Figure 16:
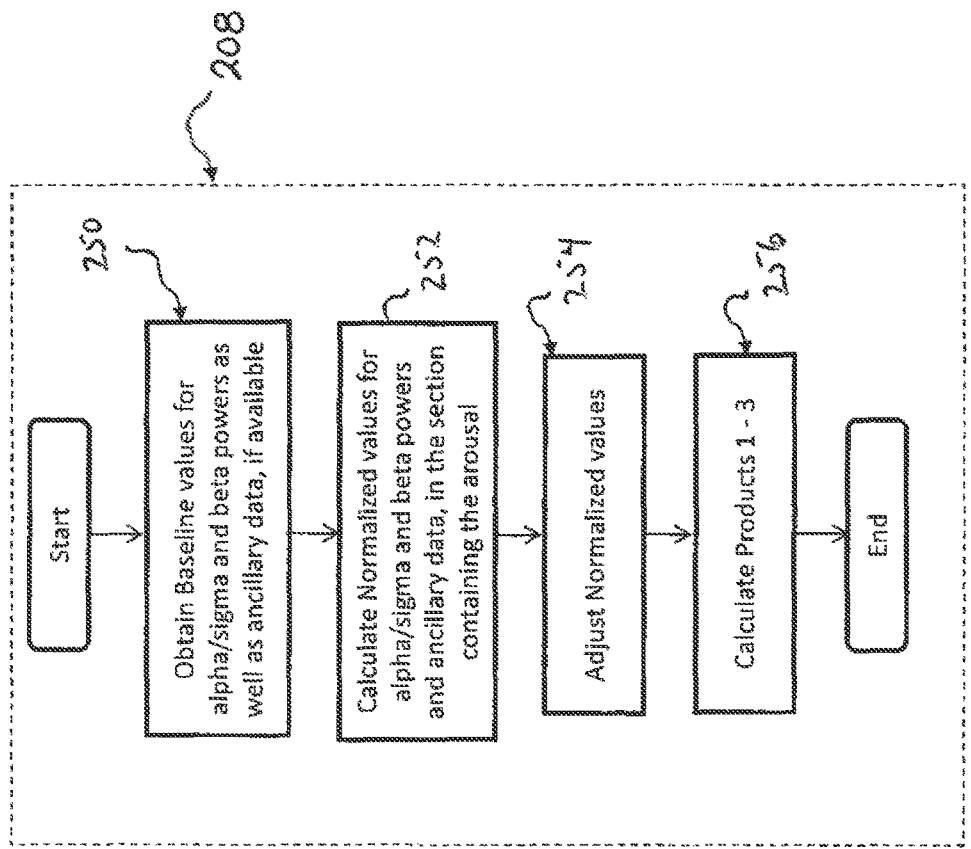
FIG. 16 is a flowchart showing the steps of a feature extraction stage forming part of the arousal intensity scoring methodology of FIG. 12.

FIG. 16 better illustrates the steps performed during feature extraction at step 208. In this embodiment five (5) variables are used to generate the features to be used in arousal intensity scoring. These five (5) variables are beta power and alpha/sigma power, obtained from the EEG signal, respiratory and chin EMG amplitudes and heart rate changes. Initially, the baseline values for each of the five (5) variables (alpha/sigma and beta powers and respiratory, chin EMG and heart rate, if available) are determined (step 250). All values within the selected baseline interval that pertain to a given variable are then sorted in ascending order. For a three (3) minute baseline interval, there are sixty (60) values for each of the five (5) variables. The lowest value (Minimum), the $50^{th}$ percentile and the $70^{th}$ percentile values are identified from each series. The baseline value for each of the five (5) variables for the entire baseline interval (2 to 5 minutes) is then calculated as the higher of the $70^{th}$ percentile value or [Minimum+1.4*($50^{th}$ percentile−Minimum)]. Minimum values are imposed on these baseline values to guard against inflated ratios when these baseline values are very low. These minimum values apply to data collected using standard calibration techniques that are filtered and processed with FFT as described above. If conditions change, these minimum values may need to be adjusted accordingly. The minimum values used in this embodiment are:

Alpha/sigma power: 3.0 $\mu V^2$. This corresponds to the $10^{th}$ percentile of all alpha/sigma power values obtained in≈400,000 three (3) second intervals from approximately sixty (60) sleep studies.

Beta power: 1.0 $\mu V^2$. This also corresponds to the $10^{th}$ percentile of all beta power values obtained in≈400,000 three (3) second intervals from approximately sixty (60) sleep studies.

Chin EMG: 0.2 units. This is approximately ¼ of the value usually observed during REM sleep.

Heart rate: 3 beats/minute.

Respiratory excursion: This varies with the recording system used. It is intended to represent the average tidal excursion of the measured signal. In this case, with use of Respitrace®, the value was 20 units.

Next, the three (3) second epochs containing the arousal segment are identified from the stored arousal segment onset and end times. All three (3) second intervals that contain part of the arousal segment are examined. For each three (3) second interval included in the arousal segment, each of the five (5) variable values is normalized (step 252) by dividing the variable value by the corresponding baseline value calculated in step 250.

Next at step 254, corrections are applied to the normalized values as follows:

If any ratio is <1.0, increase it to 1.0.

If ratio of Chin EMG, heart rate or respiratory amplitude is >2.0, reduce to 2.0. This is to avoid putting too much weight on ancillary variables.

If alpha ratio is >1.0 but alpha power <11, reset alpha ratio to 1.0.

If alpha/sigma ratio is >1.0 but <2.0 AND alpha power >30, reset alpha ratio to 2.0.

If Beta ratio is >1.0 but Beta power is <3.6, reset beta ratio to 1.0.

If Beta ratio is >2.0 but Beta power is <6.5, reset beta ratio to 2.0.

If Beta ratio is between 1.5 and 2.0 but Beta power is >6.5, reset beta ratio to 2.0.

If chin EMG ratio >1.4 but chin EMG is <1.2, reset chin EMG ratio to 1.4.

Again, those of skill in the art will appreciate that these corrections may require adjustment if the EEG signal is processed differently from what is described here.

Next combinations (products) of the above ratios are calculated (step 256) as follows:

Product-1: The product of all five ratios.

Product-2: The product of alpha/sigma and beta ratios.

Product-3: The product of the three ancillary ratios.

In this embodiment, therefore, there are a maximum of five (5) primary features, given by the ratios of alpha/sigma, beta, and three ancillary ratios each with a maximum of 2.0. The number of available features depends on the number of ancillary features available and may range from three (3) (alpha and beta ratios and product 2) to eight (8).

The final step of assigning an arousal intensity scale value to each arousal follows a procedure similar to that of the previous embodiment. The only difference is that the training data set contains different features that are FFT-based as well as features related to the ancillary variables. In this case, the training data set is constructed by analyzing each of the visually scaled arousals as described above. Because the EEG files to be examined may not contain one or more of the ancillary variables, it may be necessary to construct different training sets as follows:

A set where all eight (8) features are available

A set with one ancillary variable missing

A set with two ancillary variables missing

A set with all ancillary variables missing

The classifiers used in the previous embodiment are used in this embodiment. However, it has been found that when all eight (8) features are available Product-1, raised to the power 0.2 with a maximum of 9, agrees well with visual intensity scales.

With either of these embodiments or with other embodiments using different techniques of identifying amplitude or power of specified frequency ranges in the EEG signal, the assigned arousal intensity scale values are stored in memory to be available for display by the user.

The arousal intensity scoring programs or applications may comprise modules, routines, object components, data structures, and the like, and may be embodied as computer readable program code stored on a non-transitory computer readable medium. The non-transitory computer readable medium is any data storage device that can store data. Such non-transitory computer readable media include for example, but are not limited to, read-only memory, random-access memory, CD-ROMs, magnetic tape, USB keys, flash drives and optical data storage devices. The computer readable program code can also be distributed over a network including coupled computer systems so that the computer readable program code is stored and executed in a distributed fashion.

Although embodiments have been described with reference to the accompanying drawings, those of skill in the art will appreciate that modifications and variations may be made without departing from the scope of the appended claims.

What is claimed is:

1. A computerized method for quantifying intensity of arousal event(s) in an electroencephalogram of a subject to determine potential impact of said arousal event(s) on sleep quality and cardiovascular function, the method comprising:
   statistically analyzing, using one or more processors, at least one section of a digitally recorded electroencephalography (EEG) signal that comprises an arousal segment to determine, for the arousal segment, at least one of amplitude and power at different frequencies;
   assigning, using one or more processors, an intensity scale value to each arousal segment based on matching at least one of the determined amplitude and the power of the each arousal segment at the different frequencies to an existing reference data set to determine an arousal intensity score for said each arousal segment, said existing reference data set comprising at least one of amplitudes and powers at different EEG frequencies obtained from a plurality of arousal segments to which a range of arousal intensity scale values have been previously independently assigned visually; and
   reporting the arousal intensity score for said each arousal segment to at least one of the subject and to one or more health care professionals for use in determining the potential impact of said each arousal event on the subject's sleep quality and cardiovascular function.

2. The method of claim 1 wherein said statistically analyzing comprises statistically analyzing, using the one or more processors, a plurality of sections of the EEG signal, each section of which comprises an arousal segment, to determine, for each arousal segment, at least one of the amplitude and the power at different frequencies, and wherein said assigning comprises assigning, using the one or more processors, an intensity scale value to each arousal segment based on matching the at least one of the amplitude and the power of the each arousal segment at the different frequencies to the existing reference data set to determine the arousal intensity score for the each arousal segment.

3. The method of claim 2 wherein each of said plurality of sections comprises the arousal segment and a baseline segment, and wherein during said statistically analyzing, for each arousal segment, at least one of the amplitude and the power features from the arousal segment and associated baseline segment are extracted.

4. The method of claim 3 wherein the baseline segment associated with each arousal segment immediately precedes the arousal segment in the EEG signal.

5. The method of claim 4 wherein the baseline segment associated with each arousal segment has a duration substantially equal to the duration of the arousal segment.

6. The method of claim 3 wherein the baseline segment associated with each arousal segment at least partially encompasses the arousal segment.

7. The method of claim 6 wherein the baseline segment associated with each arousal segment fully encompasses the arousal segment.

8. The method of claim 3 wherein during the statistically analyzing, the arousal and baseline segments of each of said plurality of sections are subjected to a wavelet transform and detail and approximation coefficients are generated, and wherein at least one of the amplitude and the power features are extracted from said generated detail and approximation coefficients.

9. The method of claim 2 wherein during the statistically analyzing, the EEG signal is subjected to a Fourier transform.

10. The method of claim 2 further comprising, prior to said statistically analyzing, preprocessing the EEG signal using one or more processors.

11. The method of claim 10 wherein said preprocessing comprises subjecting said EEG signal to a notch filter and then to a low pass filter.

12. The method of claim 2 further comprising, prior to said statistically analyzing, scoring the EEG signal to identify onset and end times of arousal segments therein.

13. The method of claim 2 wherein said assigning comprises using a plurality of classifiers to map the at least one ne of the amplitude and the power of each arousal segment at said different frequencies to the reference data set and determine the intensity scale value to be assigned to each arousal segment.

14. The method of claim 6 wherein during said statistically analyzing, ancillary signals available in said EEG signal are analyzed.

15. The method of claim 14 wherein said ancillary signals comprise one or more of heart rate, respiratory amplitude and chin EMG amplitude.

16. The method of claim 2 further comprising one or more of saving, displaying, transmitting and printing the intensity scale values assigned to the arousal segments.

17. The method of claim 2 further comprising using the intensity scale values assigned to the arousal segments during preparation of a comprehensive sleep study report.

18. A non-transitory computer-readable medium embodying a computer program comprising instructions, which when executed by one or more processors, cause an apparatus at least to:
   statistically analyze at least one section of a digitally recorded electroencephalography (EEG) signal of a subject that comprises an arousal segment to determine, for the arousal segment, at least one of amplitude and power at different frequencies;
   assign an intensity scale value to each arousal segment based on matching at least one of the determined amplitude and power of the each arousal segment at the different frequencies to an existing reference data set to determine an arousal intensity score for said each arousal segment, said existing reference data set comprising at least one of amplitudes and powers at different EEG frequencies obtained from a plurality of arousal segments to which a range of arousal intensity scale values have been previously independently assigned visually; and
   reporting the arousal intensity score for said each arousal segment to the at least one of the subject and to one or more health care professionals for use in determining the potential impact of said each arousal event on the subject's sleep quality and cardiovascular function.

19. An apparatus comprising:
   memory; and
   one or more processors operatively associated with said memory and configured to execute non-transitory program instructions in said memory to cause said apparatus at least to:
      statistically analyze at least one section of a digitally recorded electroencephalography (EEG) signal of a subject that comprises an arousal segment to determine, for the arousal segment, at least one of amplitude and power at different frequencies;
      assign an intensity scale value to each arousal segment based on matching at least one of the determined amplitude and the power of the each arousal segment at the different frequencies to an existing reference data set to determine an arousal intensity score for said each arousal segment, said existing reference data set comprising at least one of amplitudes and powers at different EEG frequencies obtained from a plurality of arousal segments to which a range of arousal intensity scale values have been previously independently assigned visually; and reporting the arousal intensity score for said each arousal segment to at least one of the subject and to one or more health care professionals for use in determining the potential impact of said each arousal event on the subject's sleep quality and cardiovascular function.

20. The apparatus of claim 19 wherein the program instructions, when executed by the one or more processors, cause said apparatus at least to statistically analyze a plurality of sections of the EEG signal, each section of which comprises an arousal segment, to determine, for each arousal segment, the at least one of the amplitude and the power at different frequencies and to assign an intensity scale value to each arousal segment based on matching at least one of the amplitude and the power of the each arousal segment at the different frequencies to the existing reference data set to determine the arousal intensity score for the each arousal segment.

21. The apparatus of claim 20 wherein each of said plurality of sections comprises the arousal segment and a baseline segment, and wherein during statistically analyzing, the apparatus is caused to, for each arousal segment, extract at least one of the amplitude and the power features from the arousal segment and associated baseline segment.

* * * * *